United States Patent [19]

Wadley

[11] Patent Number: 4,765,750

[45] Date of Patent: Aug. 23, 1988

[54] METHOD OF DETERMINING SUBSURFACE PROPERTY VALUE GRADIENT

[75] Inventor: Haydn N. G. Wadley, Poolesville, Md.

[73] Assignee: The United States of America as represented by the Secretary of Commerce, Washington, D.C.

[21] Appl. No.: 31,716

[22] Filed: Mar. 26, 1987

[51] Int. Cl.[4] .............................................. G01K 11/24
[52] U.S. Cl. .................................................. 374/137
[58] Field of Search .......................... 374/117, 7, 137; 73/597, 643; 310/311, 313 B, 315

[56] References Cited

U.S. PATENT DOCUMENTS

| | | | |
|---|---|---|---|
| 2,439,130 | 4/1948 | Firestone | 73/598 |
| 3,512,400 | 5/1970 | Lynnworth | 73/598 X |
| 4,232,557 | 11/1980 | Vasile | 73/643 X |
| 4,245,500 | 1/1981 | Malang | 374/30 |
| 4,246,784 | 1/1981 | Bowen | 374/137 X |
| 4,249,418 | 2/1981 | Ebata | 3321/107 A X |
| 4,395,913 | 8/1983 | Peterson | 73/643 |
| 4,522,071 | 6/1985 | Thompson | 73/597 |
| 4,538,925 | 9/1985 | Zgonik | 374/15 X |
| 4,541,732 | 9/1985 | Shah | 374/117 |
| 4,593,567 | 6/1986 | Isselstein et al. | 73/673 |

FOREIGN PATENT DOCUMENTS

| | | | |
|---|---|---|---|
| 0857837 | 11/1979 | U.S.S.R. | 374/137 |
| 0930024 | 5/1982 | U.S.S.R. | 374/137 |

OTHER PUBLICATIONS

"Ultrasonic Testing", J. Szilard, pp. 191, 303-309, 315-317, 432-435, TA 417.4 U4, 1982.

Primary Examiner—Daniel M. Yasich
Attorney, Agent, or Firm—Thomas Zack; Alvin Englert; Douglas E. Jackson

[57] ABSTRACT

A method for determining a subsurface property value gradient of a body includes the step of generating a Rayleigh wave in the body by passing a current through a first meander coil having predetermined spaced wires determining a wavelength of the generated Rayleigh wave. A second meander coil identical to the first meander coil is spaced at a predetermined distance from the first meander coil. The Rayleigh wave is then detected with the second meander coil and the velocity of the Rayleigh wave is determined. A property value of the body is determined at a depth determined by the wavelength of the Rayleigh wave which property value is a function of the determined velocity. The above steps are then repeated with at least one other pair of first and second meander coils having different predetermined spaced wires such that at least one second property value at a second depth is determined and a subsurface property value gradient is produced. Preferably, the pairs of meander coils are mounted to respective identical bases such that the distance between respective pairs of first and second coils is the same for all of the pairs of first and second coils. In addition, the property values determined are preferably temperatures, and the step of initially determining a modulus versus temperature profile for a material of the body is performed.

3 Claims, 1 Drawing Sheet

U.S. Patent   Aug. 23, 1988   4,765,750
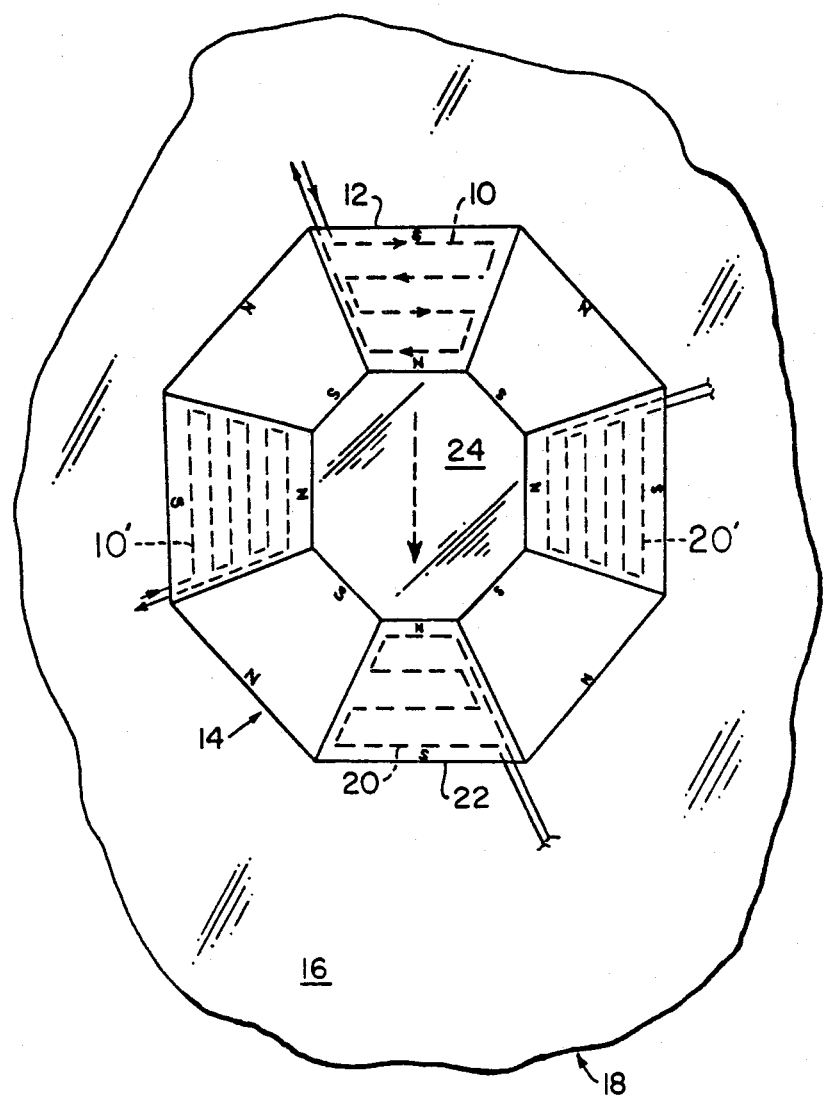

METHOD OF DETERMINING SUBSURFACE PROPERTY VALUE GRADIENT

FIELD OF THE INVENTION

The present invention relates generally to the measurement of subsurface property value gradients, and more particularly to a non-invasive method for determining subsurface temperature gradients of a body.

BACKGROUND OF THE INVENTION

An ultrasonic temperature sensor has been disclosed in U.S. Pat. No. 4,541,732 (Shah). The device disclosed in this patent makes accurate and highly sensitive temperature measurements by means of an ultrasonic wave which is caused to traverse a path which has a temperature sensitive modulus. The speed of propagation and hence the traverse time of the wave over the path is a function of temperature so that temperature can be measured by means of a time difference approach. A temperature detector using a surface acoustic wave device is disclosed in U.S. Pat. No. 4,249,418 (Ebata). The disclosed apparatus includes a signal processing circuit for processing the output of the detecting means to generate a temperature display.

In U.S. Pat. No. 4,593,567 (Isselstein et al), an electromagnetic transducer is disclosed for the transmission and reception of ultrasonic waves. The transducer is arranged for the continuous fault testing of a material by wave length spectroscopy and in particular modal spectroscopy. Another electromagnetic acoustic transducer is disclosed in U.S. Pat. No. 4,395,913 (Peterson). This fault detecting transducer utilizes plural wavelengths.

A method and apparatus for measuring stress in a material using periodic permanent magnet electromagnetic acoustic transducers is disclosed in U.S. Pat. No. 4,522,071 (Thompson).

SUMMARY OF THE INVENTION

In accordance with the present invention, a method for determining a subsurface property value such as a temperature gradient of a body having a surface is disclosed. Initially, a Rayleigh wave is generated in the body by passing a current through a first meander coil having predetermined spaced wires determining a wavelength for the generated Rayleigh wave. A second meander coil identical to the first meander coil is spaced at a predetermined distance from the first meander coil. The Rayleigh wave generated by the first meander coil is detected with the second meander coil. The velocity of the Rayleigh wave is then determined. The temperature of the body at a depth determined by the wavelength of the Rayleigh wave is then determined as this temperature is a function of the determined velocity. Finally, the above steps are repeated with at least one other pair of first and second meander coils having different predetermined spaced wires so that a second temperature in a second depth is determined and a surface temperature gradient is produced.

Preferably, each pair of first and second coils is mounted to a respective one of a plurality of identical bases. In this manner, the distance between respective pairs of first and second coils is made the same for all the pairs of first and second coils. In the preferred embodiment, a modulus versus temperature profile for a material of the body is initially determined prior to the determining steps.

It is an object of the present invention to provide a easy and efficient method for converting the modulus profile of an element to a surface temperature gradient.

Other features and objects of the present invention are stated in or apparent from a detailed description of a presently preferred embodiment of the invention found hereinbelow.

BRIEF DESCRIPTION OF THE DRAWING

The single FIGURE is a schematic top plan view of an electromagnetic acoustic transducer used for measuring the velocity of a Rayleigh wave according to the present invention.

DETAILED DESCRIPTION OF THE PREFERRED EMBODIMENT

In general, the velocity of a Rayleigh wave on the surface of a plane homogenous body is independent of frequency. However, in bodies with depth dependent modulus/density, because the Rayleigh wave penetration is wavelength dependent, Rayleigh dispersion exists. Thus, in a cooling steel slab or the like whose surface is cooler than the interior, high frequency Rayleigh waves travel at a faster velocity than low frequency waves which penetrate into the interior.

Methods exist to invert dispersion data so as to deduce the modulus depth profile such as shown in *Quantitative Seismology II* by Aki and Richards, page 711. Thus, a prior determination of modulus versus temperature relation for a particular steel grade to be interrogated can be used to convert a modulus profile to a surface temperature gradient.

According to the method of the present invention, this knowledge is implemented by using electromagnetic acoustic transduction technology as shown in the FIGURE. A meander coil 10 is placed beneath a magnetic field of an element 12 forming part of a base 14 of similar elements. Meander coil 10 is then located adjacent a surface 16 of a body 18 to be interrogated. A current passing through coil 10 results in the induction of a vertical Lorentz force in body 18. The spacing between adjacent wires of meander coil 10 determines the wavelength of the emitted Rayleigh wave where the wavelength is equal to the spacing. This wave propagates normal to the wire and is detected with a detector coil 20. Detector coil 20 is located below the magnetic field of another element 22 of base 14. A center region 24 is provided in base 14 between elements 12 and 22.

By varying the spacing between adjacent wires in other meander coil and detector coil pairs such as coil pairs 10' and 20', it is possible to propagate different wavelength Rayleigh waves. Preferably, the various coil pairs are provided on one of a plurality of identical bases 14. Then, by measuring the time of flight and knowing the propagation distance, the velocity of these Rayleigh waves is measured. A temperature profile normal to the region is then deduced.

By way of example, if the Rayleigh velocity is approximately 3 mm/us, a 10 MHz wave penetrates about 0.3 mm while a 100 KHz wave penetrates about 30 mm. Based on these figures, the dimensions of coils 10 and 20 should be such that at least 4 to 8 wires (i.e., 2 to 4 wavelengths) are below each respective element 12 and 22. Thus, to penetrate 1 inch, a base approximately 4 to 6 inches in width would be suitable.

Although the present invention has been described as suitable for determining the temperature gradient in a body, it should be appreciated that a variety of properties of an object which vary with penetration may similarly be measured. Among such properties are compositional and microstructure gradients, the depth of cracks, and surface roughness. Thus, while the present invention has been described with respect to an exemplary embodiment thereof, it will be understood by those of ordinary skill in the art that variations and modifications can be effected within the scope and spirit of the invention.

I claim:

1. A method for determining a subsurface property value gradient of a body having a surface comprising the steps of:

generating a Rayleigh wave in the body by passing a current through a first meander coil having predetermined spaced wires determining a wavelength of the generated Rayleigh wave;

spacing a second meander coil identical to the first meander coil at a predetermined distance from the first meander coil;

detecting the Rayleigh wave with the second meander coil;

determining the velocity of the Rayleigh wave;

determining a property value at a depth determined by the wavelength of the Rayleigh wave which property value is a function of the determined velocity;

repeating the above steps with at least one other pair of first and second meander coils having different predetermined spaced wires than the first-mentioned pair of first and second meander coils such that at least one second property value at a second depth is determined; and determining a subsurface property value gradient from the first-mentioned property value and the at least one second property value.

2. A method for determining a subsurface property value gradient as claimed in claim 1 and further including the steps of mounting each pair of first and second coils to respective identical bases such that the distance between respective pairs of first and second coils is the same for all the pairs of first and second coils.

3. A method for determining a subsurface property value gradient as claimed in claim 1 wherein the property values determined are temperatures, and further including the step of initially determining a modulus versus temperature profile for a material of the body.

* * * * *